(12) United States Patent
Franklin et al.

(10) Patent No.: US 7,910,597 B2
(45) Date of Patent: Mar. 22, 2011

(54) SUBSTITUTED QUINAZOLINES

(75) Inventors: Richard Franklin, Hampshire (GB); Bernard T. Golding, Newcastle upon Tyne (GB)

(73) Assignee: Shire LLC, Florence, KY (US)

( * ) Notice: Subject to any disclaimer, the term of this patent is extended or adjusted under 35 U.S.C. 154(b) by 223 days.

(21) Appl. No.: 11/946,572

(22) Filed: Nov. 28, 2007

(65) Prior Publication Data

US 2008/0176877 A1 Jul. 24, 2008

Related U.S. Application Data

(60) Provisional application No. 60/861,458, filed on Nov. 28, 2006.

(51) Int. Cl.
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ...................... 514/267; 544/250

(58) Field of Classification Search .............. 514/267; 544/250
See application file for complete search history.

(56) References Cited

U.S. PATENT DOCUMENTS

| | | |
|---|---|---|
| 1,947,926 A | 2/1934 | Steindorff et al. |
| 2,256,999 A | 9/1941 | Castner |
| 2,469,695 A | 5/1949 | McNally |
| 2,608,584 A | 8/1952 | Sprules et al. |
| 2,732,403 A | 1/1956 | Surrey |
| 2,862,966 A | 12/1958 | Surrey |
| 2,883,435 A | 4/1959 | Welch |
| 3,313,854 A | 4/1967 | Levy |
| 3,928,476 A | 12/1975 | Shimada et al. |
| 3,932,407 A | 1/1976 | Beverung, Jr. et al. |
| 3,983,119 A | 9/1976 | Beverung, Jr. et al. |
| 3,983,120 A | 9/1976 | Beverung et al. |
| 3,988,340 A | 10/1976 | Partyka et al. |
| 4,036,838 A | 7/1977 | Vogel et al. |
| 4,048,168 A | 9/1977 | Yamamoto et al. |
| 4,146,718 A | 3/1979 | Jenks et al. |
| 4,179,560 A | 12/1979 | Yamamoto et al. |
| 4,202,974 A | 5/1980 | Yamamoto et al. |
| 4,208,521 A | 6/1980 | Crenshaw et al. |
| 4,256,748 A | 3/1981 | Chodnekar et al. |
| 4,357,330 A | 11/1982 | Fleming, Jr. et al. |
| 4,390,540 A | 6/1983 | Chodnekar et al. |
| 4,444,777 A | 4/1984 | Fleming, Jr. et al. |
| RE31,617 E | 6/1984 | Beverung, Jr. et al. |
| 4,455,311 A | 6/1984 | Kienzle et al. |
| 4,610,987 A | 9/1986 | Ishikawa et al. |
| 4,808,405 A | 2/1989 | Smith et al. |
| 4,837,239 A | 6/1989 | Benjamin et al. |
| 4,847,276 A | 7/1989 | Yarrington |
| 5,043,327 A | 8/1991 | Freyne et al. |
| 5,133,972 A | 7/1992 | Ferrini et al. |
| 5,306,709 A | 4/1994 | Gewirtz |
| 5,334,384 A | 8/1994 | Mannix et al. |
| 5,391,737 A | 2/1995 | Reiter et al. |
| 5,801,245 A | 9/1998 | Lang |
| 5,874,437 A | 2/1999 | Garvey et al. |
| 6,024,975 A | 2/2000 | D'Angelo et al. |
| 6,037,346 A | 3/2000 | Doherty, Jr. et al. |
| 6,110,471 A | 8/2000 | Conti et al. |
| 6,156,753 A | 12/2000 | Doherty, Jr. et al. |
| 6,194,420 B1 | 2/2001 | Lang |
| 6,221,383 B1 | 4/2001 | Miranda et al. |
| 6,297,243 B1 | 10/2001 | Groendahl et al. |
| 6,299,900 B1 | 10/2001 | Reed et al. |
| 6,331,543 B1 | 12/2001 | Garvey et al. |
| 6,376,242 B1 | 4/2002 | Hanson |
| 6,388,073 B1 | 5/2002 | Lang et al. |
| 6,403,597 B1 | 6/2002 | Wilson et al. |
| 6,548,490 B1 | 4/2003 | Doherty, Jr. et al. |
| 6,548,529 B1 | 4/2003 | Robl et al. |
| 6,585,995 B1 | 7/2003 | Hanson |
| 6,653,500 B2 | 11/2003 | Lang et al. |
| 2002/0004065 A1 | 1/2002 | Kanios |
| 2002/0004498 A1 | 1/2002 | Doherty et al. |
| 2003/0114673 A1 | 6/2003 | Lang |
| 2003/0134861 A1 | 7/2003 | Doherty et al. |
| 2003/0181461 A1 | 9/2003 | Lautt et al. |
| 2004/0014761 A1 | 1/2004 | Place et al. |

(Continued)

FOREIGN PATENT DOCUMENTS

AT 2732004 8/2005

(Continued)

OTHER PUBLICATIONS

Wang, et al., Comparison of the biological activities of anagrelide and its major metabolites in haematopoietic cell cultures, British J. of Pharmacology, 146, 324-332 (2005).*
Agrylin Monograph—Shire 2003—10.
Cohen-Solal et al., Thromb. Haemost. 1997, 78:37-41 -p. 18, l 31 of 5096 and p. 27, I 9 of 3796.
Cramer et al., Blood, 1997, 89:2336-46-p. 18, I 31 of 5096 and p. 27, I 9 of 3796.
Kienzle et al., "1,5-Dihydroimidazoquanizolinones as blood platelet aggregation inhibitors," Eur. J. Med. Chem. Chim. Ther., 1982, 17:547-556.
Kienzle et al., "Die synthese von 2,3,4,5-1Htetrahydroimidazo-[2,1-b]chinazolin-2,5-dionen und analogen 2,3,4,5-1H-tetrahydroimidazo[1,2-a]thieno[2,3-d](bzw. [3,2-d])-pyrimidin-2,5-dionen," Helv. Chim. Acta, 1983, 66:148-157.

(Continued)

*Primary Examiner* — James O Wilson
*Assistant Examiner* — Erich A Leeser
(74) *Attorney, Agent, or Firm* — Shelly M. Fujikawa; Frommer Lawrence & Haug LLP

(57) ABSTRACT

This invention relates to the discovery of 3- and 5-substituted analogues of the selective platelet lowering agent anagrelide with reduced potential for cardiovascular side-effects which should lead to improved patient compliance and safety in the treatment of myeloproliferative diseases. More specifically, the present invention relates to certain imidazoquinazoline derivatives which have utility as platelet lowering agents in humans. The compounds of the present invention function by inhibiting megakaryocytopoeisis and hence the formation of blood platelets.

5 Claims, No Drawings

U.S. PATENT DOCUMENTS

| | | | |
|---|---|---|---|
| 2004/0087486 A1 | 5/2004 | Hanson | |
| 2004/0087546 A1 | 5/2004 | Zeldis | |
| 2004/0209907 A1* | 10/2004 | Franklin | 514/266.22 |
| 2005/0049293 A1 | 3/2005 | Lautt | |
| 2005/0119272 A1 | 6/2005 | Lautt et al. | |
| 2005/0228001 A1 | 10/2005 | Hanson | |
| 2006/0030574 A1 | 2/2006 | Franklin | |
| 2006/0052601 A1* | 3/2006 | Franklin | 544/250 |
| 2006/0148832 A1 | 7/2006 | Sachse | |
| 2006/0292213 A1 | 12/2006 | Gerber et al. | |
| 2007/0099819 A1 | 5/2007 | Glidden | |

FOREIGN PATENT DOCUMENTS

| | | | |
|---|---|---|---|
| CA | 2150033 | | 6/1994 |
| DE | 2832138 A1 | | 2/1979 |
| DE | 19935209 | | 2/2001 |
| EP | 0 021 338 | | 1/1981 |
| EP | 0046267 | | 2/1982 |
| EP | 0054180 | | 6/1982 |
| EP | 0 153 152 | | 8/1985 |
| EP | 0 205 280 | | 12/1986 |
| EP | 0 406 958 | | 1/1991 |
| EP | 0 514 917 | | 11/1992 |
| EP | 0 546 697 | | 6/1993 |
| EP | 994114 A2 | | 4/2000 |
| GB | 2001638 | * | 2/1979 |
| JP | S42-17893 | | 9/1967 |
| JP | S42 17893 | | 9/1967 |
| JP | S47-19261 | | 6/1972 |
| JP | 01258658 | | 10/1989 |
| WO | WO-9308798 | | 5/1993 |
| WO | WO-9309794 | | 5/1993 |
| WO | WO-9428902 | | 12/1994 |
| WO | WO-9616644 | | 6/1996 |
| WO | WO-9810765 | | 3/1998 |
| WO | WO-9938496 | | 8/1999 |
| WO | WO-0048636 | | 8/2000 |
| WO | WO-0121163 | | 3/2001 |
| WO | WO-0121259 | | 3/2001 |
| WO | WO-0140196 | | 6/2001 |
| WO | WO-0141807 | | 6/2001 |
| WO | WO-02/08228 | | 1/2002 |
| WO | WO-02062322 | | 8/2002 |
| WO | 02096435 A2 | | 12/2002 |
| WO | WO-03000343 | | 1/2003 |
| WO | WO-03061638 | | 7/2003 |
| WO | WO-03061648 | | 7/2003 |
| WO | WO-2004012700 | | 2/2004 |
| WO | WO-2004037262 | | 5/2004 |
| WO | WO-2004043336 | | 5/2004 |
| WO | WO-2004043464 | | 5/2004 |
| WO | WO-2004/063172 | | 7/2004 |
| WO | WO-2004064841 | | 8/2004 |
| WO | WO-2005025570 | | 3/2005 |
| WO | WO-2005048979 | | 6/2005 |
| WO | WO-2005065639 | | 7/2005 |
| WO | WO-2006017822 | | 2/2006 |
| WO | WO 2010/005480 | | 1/2010 |

OTHER PUBLICATIONS

Martinez et al., "3,4-Dihydroquinolin-2(1H)-ones as combined inhibitors of thromboxane A2 synthase and cAMP phosphodiesterase." J. Med. Chem., 1992, 35:620-628.

Meanwell et al., "1,3-Dihydro-2H-imidazo[4,5-b]quinolin-2-ones—inhibitors of blood platelet cAMP phosphodiesterase and induced aggregation." J. Med. Chem., 1991, 34:2906-2916.

Meanwell et al., "Inhibitors of blood platelet cAMP phosphodiesterase. 2. Structure-activity relationships associated with 1,3-dihydro-2H-imidazo[4,5-b]quinolin-2-ones substituted with functionalized side chains." J. Med. Chem., 1992, 35: 2672-2687.

Stalder, "Metaboliten der 1,5-dihydroimidazo[2,1-b]chinazolin-2(3H)-one. Synthese und reaktionen einiger 1,5-dihydro-3-hydroxyimidazo[2,1-b]chinazolin-2(3H)-one," Helv. Chim. Acta, 1986, 69:1887-1897.

Venuti et al., "Inhibitors of cyclic AMP phosphodiesterase. 2. Structural variations of N-cyclohexyl-N-methyl-4-[(1,2,3,5-tetrahydro-2-oxoimidazo[2,1-b]quinazolin-7-yl)-oxy]butyramide (RS-82856)." J. Med. Chem., 1987, 30:303-318.

Venuti et al., "Inhibitors of cyclic AMP phosphodiesterase. 3. Synthesis and biological evaluation of pyrido and imidazolyl analogues of 1,2,3,5-tetrahydro-2-oxoimidazo[2,1- b]quinazoline." J. Med. Chem., 1988, 31:2136-2145.

Citizen Petition, Arnall Golden Gregory LLP, Aug. 13, 2004, 159 pages.

Wagstaff, Antona J. et al., Anagrelide: A Review of its Use in the Management of Essential Thrombocythaemia, Drugs 2006, 66(1):111-131.

Wang, Guosu, et al., "Comparison of the Biological Activities of Anagrelide and its Major Metabolites in Haematopoietic Cell Cultures," British Journal of Pharmacology 2005, 146:324-332.

Bell, Andrew S., et al. "7-Heteroaryl-1,2,3,5-tetrahydroimidazo[2,1-b]quinazolin-2(1H)-one Derivatives with Cardiac Stimulant Activity," Journal of Medicinal Chemistry, 1989, vol. 32, No. 9, pp. 2042-2049 (8 pages).

Kienzle, Frank, et al. "1,5-Dihydroimidazoquinazolinones as Blood Platelet Aggregation Inhibitors," European Journal of Medicinal Chemistry, 1982-17, No. 6, pp. 546-556 (10 pages).

Imidazo[2,1-b]quinazolin-2(3H)-one, 1,5-dihydro-3,3-dimethyl-,monohydrochloride (9CI), as referenced in European Journal of Medicinal Chemistry (1982), 17(6), 547-56 (1 page).

Imidazo[2,1-b]quinazolin-2(3H)-one, 1,5-dihydro-3,3,6-trimethyl-, monohydrochloride (9CI), as referenced in European Journal of Medicinal Chemistry (1982), 17(6), 547-56 (1 page).

Imidazo[2,1-b]quinazolin-2(3H)-one, 1,5-dihydro-3,3,6-trimethyl-, as supplied by Chemstep, France. Catalog Publication Date Jun. 19, 2007 (1 page).

Imidazo[2,1-b]quinazolin-2(3H)-one, 1,5-dihydro-3,3-dimethyl-, as supplied by Chemstep, France. Catalog Publication Date Jun. 19, 2007 (1 page).

Signed Declaration pursuant to 37 C.F.R. §1.132 by Dr. Richard Franklin submitted in U.S. Appl. No. 10/762,566, filed Sep. 19, 2007 and Exhibit 1 to the Declaration (the curriculum vitae for Dr. Richard Franklin), 8 pgs.

Agrylin (anagrelide hydrochloride), Product Monograph, Roberts Pharmaceutical Corp.; 1997.

Aldrich Catalogue 1996, p. 498.

Andes et al "Inhibition of platelet production induced by an antiplatelet drug, anagrelide, in normal volunteers, " Thromb. Haemost., 1984, 52:325-8.

Barbui, Tiziano, et al. "Practice guidelines for the therapy of essential thrombocythemia," p. 215.

"Blood," Journal of the American Society of Hematology; W. R. Saunders Company; vol. 94; No. 10; Supplement 1 (Part 1 of 2); Nov. 15, 1999; p. 701a.

Decision on FDA Citizen Petition No. 2004P-0365 by the FDA, Apr. 18, 2005.

Doherty, "Oral, Transdermal and Transurethral Therapies for Erectile Dysfunction" in Male Infertility and Dysfunction, Ch. 33, 1997.

Dörwald, F. Zaragoza. "Side Reactions in Organic Synthesis: A Guide to Successful Synthesis Design," Weinheim: Wiley-VCH Verlag GmbH & Co. KGaA, 2005, Preface.

Erusalimsky, Jorge et al, Is the platelet lowering activity of anagrelide mediated by its major metabolite 2-amino-5 6-dichloro-3,4-dihydroquinazoline (RL603)?, Experimental Hematology, 2002, vol. 30, No. 7, pp. 625-626.

European Agency for the Evaluation of Medicinal Products (EMEA): Scientific Discussion of European Public Assessment Report (EPAR) Xagrid [http://www.emea.eu.int/humandocs/PDFs/EPAR/Xagrid/136504en6.pdf].

FDA Citizen Petition No. 2004P-0365 on behalf of Shire US, Inc., Aug. 13, 2004.

Response to FDA Citizen Petition No. 2004P-0365 by Barr Laboratories, Inc., Oct. 20, 2004.

Response to FDA Citizen Petition No. 2004P-0365 by Mylan Phermaceuticals, Inc., Sep. 8, 2004.

Gaver et al, "Disposition of anagrelide, an inhibitor of platelet aggregation." Clin. Pharmacol. Ther., 1981, 29:381-386.

Green et al., "Management of the myeloproliferative disorders: distinguishing data from dogma," Hematol. J., 2004, 5 Suppl. 3:S126-S132.

Griesshammer, Martin et al. "Current treatment practice for essential thrombocythaemia in adults" Exp. Opin. Pharmacother., 2001, 2: 385-393.

International Search Report in connection with International Application No. PCT/CA2004/000096, dated Jun. 23, 2004.

International Search Report for PCT/US05/28086 mailed Jun. 14, 2006.

Jones et al., "Inhibitors of cyclic AMP phosphodiesterase. 1. Analogues of cilostamide and anagrelide," J. Med. Chem., 1987, 30:295-303.

Jordan, V.C. "Nature Reviews: Drug Discovery," 2, 2003, p. 205.

Kelly et al., "Pharmacological treatment of heart failure," in Goodman and Gilman, Ch. 34, 1996.

Lane, William et al, "Anagrelide metabolite induces thrombocylopenia in mice by inhibitingmegakaryocyte maturation without inducing platelet aggregation," Experimental Hematology, 2001, vol. 29, No. 12, pp. 1417-1424.

Lane, William et al, "Anagrelide metabolite induces thrombocylopenia in mice by inhibition of megakaryocyte Maturation and Endoreplication without inducing platelet aggregation." Blood, 94:701a Supp. 1 (Part 1 of 2) [Abstract #3097].

Mazur et al "analysis of the mechanism of anagrelide-induced thrombocytopenia in humans" Blood, 1992, 79:1931-1937.

Morrison & Boyd, "Organic Chemistry," 3rd Ed. 1975, 344-347; 387-388.

Oertel, "Anagrelide, a selective thrombocytopenic agent." Am. J. Health Syst. Pharm., 1998, 55:1979-86.

Osinski, M., et al. "Inhibition of platelet-derived growth factor-induced mitogenesis by phosphodiesterase 3 inhibitors: Role of protein kinase A in vascular smooth muscle cell mitogenesis," Biochemical Pharmacology 2000, vol. 60, No. 3, pp. 381-387.

Pescatore, Scott et al. "Anagrelide: a novel agent for the treatment of myeloproliferative disorders," Exp. Opin. Pharmacother., 2000, 1: 537-546.

Petitt et al "Anagrelide for control of thrombocythemia in polycythemia and other myeloproliferative disorders." Semin. Hematol., 1997, 34:51-4.

Petrides, P., et al. "Anagrelide, a Novel Platelet Lowering Option in Essential Thrombocythaemia: Treatment Experience in 48 Patients in Germany," European Journal of Haematology, vol. 61, 1998, p. 71-76.

Rafii Shahin et al. "Is the platelet lowering activity of anagrelide mediated by its major metabolite 2-amino-5 6-dichloro-3,4-dihydroquinazoline (RL603)? in Response," Experimental Hematology, vol. 30, No. 7, pp. 626-627.

Solberg Jr, et al, "The effects of anagrelide on human megakaryocytopoiesis," British Journal of Haematology 1997, vol. 99, No. 1, pp. 174-180.

Souhami, R.L., et al., "Textbook of Internal Medicine," Churchill-Livingstone, p. 1043, table 25.53.

Spencer and Brogden, "anagrelide. A review of its pharmacodynamic and pharmacokinetic properties, and therapeutic potential in the treatment of thrombocythaemia." Drugs, 1994 47:809-22.

Storen, Elizabeth et al. "Long-term use of anagrelide in young patients with essential thrombocythemia," Blood, Feb. 15, 2001, vol. 97, No. 4, 863-866.

Tefferi, A., et al., "Spotlight Review—Classification and Diagnosis of myeloproliferative neoplasms: The 2008 World Health Organization criteria and point-of-care diagnostic algorithms," 2008 Nature Publishing Group. Table 1.

Trapp et al, "Anagrelide for treatment of patients with chronic myelogenous leukemia and a high platelet count." Blood Cells Mol. Dis., 1998, 24:9-13.

Vippagunta, S., et al. "Advanced Drug Delivery Reviews," 48, 2001, p. 18.

Ammar, et al., "Design of a Transdermal Delivery system for Aspirin as an Antithrombotic Drug," International Journal of Pharmaceutics, vol. 327, pp. 81-88 (2006.).

Solberg, "Therapeutic Options for Essential Thrombocythemia and Polycythemia Vera," Seminars in Oncology, vol. 28, Issue 3, Supplement 10, p. 10-15 (2002).

Bonkovsky, et al., "Drug-Induced Liver Injury," Zakim and Boyer's Hepatology, 5th Edition, p. 503 (2006).

Brown, L., et al., "Transdermal Delivery of Drugs," Annual Review of Medicine, 1988, pp. 221-229, vol. 39.

Kshirsagar, N.A., "Drug Delivery Systems," Indian Journal of Pharmacology, 2000, pp. S54-S61, vol. 32.

Tomer, A., "Effects of anagrelide on in vivo megakaryocyte proliferation and maturation in essential thrombocythemia," Blood, Mar. 2002, pp. 1602-1609, vol. 99.

\* cited by examiner

SUBSTITUTED QUINAZOLINES

This application claims priority to U.S. Provisional Application Ser. No. 60/861,458 filed Nov. 28, 2006; the contents of which are incorporated by reference in their entirety.

FIELD OF THE INVENTION

This invention relates to the discovery of 3- and 5-substituted analogues of the selective platelet lowering agent anagrelide with reduced potential for cardiovascular side-effects which should lead to improved patient compliance and safety in the treatment of myeloproliferative diseases. More specifically, the present invention relates to certain imidazoquinazoline derivatives which have utility as platelet lowering agents in humans. The compounds of the present invention function by inhibiting megakaryocytopoeisis and hence the formation of blood platelets.

BACKGROUND OF THE INVENTION

Anagrelide hydrochloride (Agrylin®, Xagrid®) is a novel orally administered imidazoquinazoline which selectively reduces platelet count in humans and is used for such purposes in the treatment of myeloproliferative diseases (MPDs), such as essential thrombocythemia (ET), where an elevated platelet count may put the patient at increased thrombotic risk. The chemical structure of anagrelide, 6,7-dichloro-1,5-dihydroimidazo[2,1-b]-quinazolin-2(3H)-one hydrochloride monohydrate is shown as the hydrochloride monohydrate in the following formula:

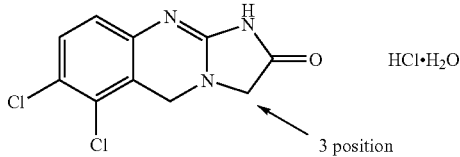

Preparation of anagrelide hydrochloride was referred to in U.S. Pat. Nos. 3,932,407; RE31,617 and 4,146,718.

Anagrelide is a unique, highly selective platelet lowering agent. In vitro studies of human megakaryocytopoiesis suggested that, in vivo, its thrombocytopenic activity results primarily from an inhibitory effect on megakaryocyte maturation. Anagrelide inhibited TPO-induced megakaryocytopoiesis in a dose-dependent manner with an estimated $IC_{50}$ of ~26 nM, showing it to be a highly potent agent. Anagrelide does not affect erythroid or myelomonocytic differentiation stimulated by erythropoietin or granulocyte-macrophage colony-stimulating factor, demonstrating the selectivity of this compound against the megakaryocytic lineage.

The drug, which is available in both the U.S. and Europe, has proven to be of considerable clinical value in the treatment of myeloproliferative diseases, such as essential thrombocythemia. Anagrelide was shown to be effective and selective in reducing and maintaining platelet count close to or within the physiological range in patients with thrombocythemia secondary to a myeloproliferative disorder. The time to complete response, defined as a platelet count $\leq 600 \times 10^9$/L, ranged from 4 to 12 weeks. In the majority of patients, the platelet count can be reduced and maintained at a dose of 1 to 3 mg/day.

In early volunteer trials, the most frequently reported adverse effects AEs other than headache were palpitations, postural dizziness and nausea. During patient studies, the most frequently reported drug-related AEs were headache, palpitations, oedema/fluid retention, nausea/vomiting, diarrhea, dizziness and abdominal pain. These effects are all likely to arise from the secondary, cardiovascular pharmacology associated with anagrelide resulting from its inhibitory effects on human phosphodiesterase III (PDE III). Anagrelide is a potent PDE III inhibitor with an $IC_{50}$ value of ~29 nM (cf. milrinone, a classical PDE III inhibitor, $IC_{50}$=170-350 nM). Inhibition of myocardial PDE III leads to positive inotropy (increasing of the force of contractions of the heart), increased chronotropy (increase in heart rate), and peripheral vasodilatation. Such cardiovascular manifestations of this inhibition are typically seen with the classical positive inotropes, milrinone and enoximone, and exploited in the short-term acute treatment of congestive heart failure. However, in the treatment of a so-called silent disease (i.e., asymptomatic) such as ET, the cardiovascular side-effects of palpitations and tachycardia associated with anagrelide limit its utility and a significant proportion of patients—reportedly between 25 and 50%—fail to tolerate the drug during long term treatment.

The PDE III inhibitory properties of anagrelide are quite distinct from its platelet lowering anti-megakaryocytic effects. Indeed studies have shown no correlation between potency as a PDE III inhibitor and anti-megakaryocytic effects for anagrelide and its principal pharmacologically active metabolite, 3-hydroxyanagrelide (3-OH anagrelide or 3-HA, formerly known as SPD604 or BCH24426). Surprisingly the latter was found to be over 40-fold more potent than anagrelide as a PDE III inhibitor. With respect to inhibition of megakaryocytopoiesis (and therefore platelet lowering potential) it was however no more potent than the parent drug. Anagrelide's active metabolite, 3-HA, is present in vivo in amounts greatly exceeding those of the parent drug with typical exposures being 2-3 fold greater. Thus by implication 3-OH anagrelide is likely to be a major contributor to the pharmacological actions of the drug.

In addition to the unwanted cardiovascular effects associated with PDE III inhibition, the consequent elevation of cAMP can result in an anti-aggregatory effect. While initially this property may appear to be beneficial in essential thrombocythemia patients predisposed to greater thrombotic risk, such anti-platelet effects, in excess, could have haemorrhagic consequences and on balance may not be desirable. Indeed the haemorrhagic events occasionally seen in ET patients treated with anagrelide might be due to a combination of the anti-aggregatory effects contributed largely by 3-OH anagrelide and an overshooting of platelet reduction, compounded by a synergistic interaction with aspirin that is frequently concomitantly administered. (In some ET patients, plasma concentrations of 3-OH anagrelide have been shown likely to exceed the in vitro $IC_{50}$ values for inhibition of platelet aggregation by a factor of 3).

The PDE III mediated cardiovascular side-effects associated with anagrelide treatment mean that many patients have to be switched to the only significant alternative therapy, namely that with hydroxyurea. However, this drug is a simple chemical anti-metabolite which inhibits ribonucleoside diphosphate reductase (RNR) with resultant profound effects on DNA synthesis. Ribonucleoside diphosphate reductase catalyzes the conversion of ribonucleosides into deoxyribonucleosides, which are the building blocks of DNA synthesis and repair. Inhibition of ribonucleoside diphosphate reductase explains the cytoreductive and—most importantly—the mutagenic effects of this compound as well as its platelet lowering action. Hydroxyurea is thus officially classified as a "presumed human carcinogen." As well as possessing the potential to induce leukemic transformation, hydroxyurea is associated with the induction of difficult-to-treat leg ulcers.

Faced with this dilemma in treatment options, there is a clear need for a new agent in the treatment of thrombocythemia which is selective in its effects on megakaryocytopoiesis but with reduced or minimal side effects. While anagrelide offers some selectivity in its mechanism of action, the limitations to its use are those associated with cardiovascular effects resulting from its secondary pharmacology and contributed largely by the active metabolite of anagrelide, 3-hydroxyanagrelide.

The metabolism of anagrelide generally proceeds extremely rapidly, resulting in a less than ideal pharmacokinetic profile of the drug. The typical half-life of anagrelide is just 1.5 hr (2.5 hr for the metabolite) necessitating frequent drug administration (up to 4 times per day). This, combined with the side-effects profile, can lead to poor patient compliance. Furthermore, anagrelide undergoes a large first pass effect (>50%) leading to considerable intersubject variation in achieved exposures and, therefore, potentially variable drug response. Also, exposure to the pharmacologically active metabolite varies dramatically between patients since its formation is dependent on CYP1A, an enzyme whose expression is highly dependent on exposure to inducing agents such as cigarette smoke. Overall, this may result in the need for careful dose titration in patients being treated with anagrelide.

U.S. Pat. No. 4,256,748 discloses a number of imidazo[2,1-b]quinazolin-2(3H)-ones which have an analogous structure to anagrelide and which are said to be effective in the treatment of thromboses resulting from their anti-aggregatory effects on blood platelets mediated by PDE III inhibition. However, this disclosure does not appreciate the entirely separate anti-megakaryocytic potential (reducing platelet numbers) which could be associated with some analogues.

Ideally there is a need for compounds which possess anti-megakaryocytic activity whilst at the same time having a reduced level of PDE III inhibitory activity and therefore unwanted cardiovascular effects.

It is an aim of the present invention to overcome various disadvantages of or to improve on the properties of prior art compounds. Thus it is an aim of the invention to provide an anagrelide derivative which has improved activity and/or reduced cardiovascular toxicity relative to prior art compounds in the treatment of diseases for which modulation of megakaryocytopoeisis provides an efficacious treatment. The compounds of the present invention are especially beneficial because they display less inhibitory activity towards phosphodiesterase III (PDE III) and yet surprisingly still retain their anti-megakaryocytic and hence platelet lowering properties.

It is also desirable that the compounds of the present invention should have an improved pharmacokinetic profile to aid patient compliance and ensure consistency of therapeutic response. It is thus a further aim to provide compounds with a good duration of action i.e. long half-life in vivo. Additionally it is a further aim to provide compounds that are available via relatively convenient synthetic processes.

The compounds described in relation to the present invention satisfy some or all of the above aims.

SUMMARY OF THE INVENTION

We have found that analogues of anagrelide in which the principal site of metabolism is blocked by an appropriate group are likely not only to have improved pharmacokinetics but also a better side effect profile. This would be expected to lead to better tolerability and improved patient compliance enabling a broader spectrum of patients to be effectively treated.

The compounds of the present invention are surprisingly beneficial for two reasons: they have a dramatically lower PDE III inhibitory activity than 3-hydroxyanagrelide, yet still retain potent anti-megakaryocytic activity. Indeed these compounds have therapeutic indices which are likely to be much more favorable than that for anagrelide itself.

In one embodiment, the present invention encompasses an anagrelide analogue comprising a 3-, 5-, 3,3- or 5,5-substituted anagrelide compound. Thus, for example, in the 3-substituted derivatives, first pass metabolism to 3-hydroxyanagrelide is effectively blocked. Surprisingly, these compounds still show good antimegakaryocytic activity. Thus one aspect of this invention relates to anagrelide analogues, comprising 3-substituted derivatives, wherein first pass metabolism to the corresponding 3-hydroxyanagrelide is effectively blocked. In the case of the 5-substituted compounds it is expected that a bulky group is more effective than a smaller group. Groups such as t-butyl and other bulky blocking groups are thus expected to be of most utility when substituted at the 5-position. A substituent comprising a large group at the 5-position is expected to sterically hinder access to the 3-position by the metabolising cytochrome's active site. This should inhibit formation of the cardioactive metabolite, 3-hydroxyanagrelide.

According to one aspect of the present invention, there is provided a compound of Formula (I) or a pharmaceutically acceptable salt or solvate thereof.

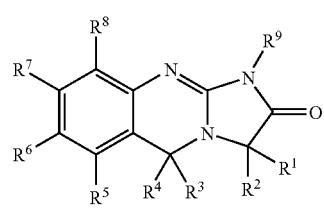

(I)

wherein:
$R^1$, $R^2$, $R^3$ and $R^4$ independently represent hydrogen or a blocking group which functions to directly or indirectly prevent metabolic reaction at the 3-position of substitution;
or wherein $R^1$ and $R^2$, and/or $R^3$ and $R^4$ together with the carbon to which they are attached form a blocking group which functions to directly or indirectly prevent metabolic reaction at either the 3-position of substitution, the remainder of groups $R^1$ to $R^4$ being hydrogen;

$R^5$ is selected from the group comprising: fluoro, chloro, bromo and iodo;

$R^6$ is selected from the group comprising: fluoro, chloro, bromo and iodo;

$R^7$ and $R^8$ are independently selected from the group comprising: H; halo; cyano; $C_{1-6}$ alkyl, $C_{1-6}$ haloalkyl, $C_{1-6}$ alkoxy, and $C_{1-6}$ haloalkoxy; and $R^9$ is H, $C_{1-6}$ alkyl, or a Group I metal ion;

provided always that $R^1$, $R^2$, $R^3$ and $R^4$ are not all hydrogen, or that when one of $R^1$ and $R^2$ is methyl and $R^3$ and $R^4$ are hydrogen then other of $R^1$ and $R^2$ is not hydrogen.

In an embodiment:

$R^1$ and $R^2$ are independently selected from the group comprising: H; cyano; $C_{1-6}$ alkyl, $SC_{1-6}$ alkyl, $C_{2-6}$ alkenyl, $C_{2-6}$ alkynyl, $C_{3-8}$ cycloalkyl wherein said alkyl, alkenyl, alkynyl or cycloalkyl groups may be optionally substituted by 1 to 5 groups chosen independently from the group comprising: halo, hydroxyl, cyano, nitro, $C_{1-4}$ alkylsulphonyl and COOH; $C_{1-6}$ hydroxyalkyl; $C_{1-6}$ carboxyalkyl; and sulphide;

or $R^1$ and $R^2$ together with the carbon to which they are attached form a $C_{3-8}$ carbocyclic ring which may be optionally substituted by 1 to 5 groups chosen independently from the group comprising: halo, hydroxyl, cyano, nitro, $C_{1-4}$ haloalkyl, $C_{1-4}$ alkylsulphonyl and COOH;

or $R^1$ and $R^2$ together represent a $C_{2-6}$ alkenyl or $C_{2-6}$ alkynyl group bound through a double bond to the ring to which it is attached and which may be optionally substituted by one to three groups independently selected from the group comprising: halo, hydroxyl, cyano, $C_{1-4}$ haloalkyl and COOH.

In a preferred set of compounds, $R^1$ is an optionally substituted $C_{1-4}$ alkyl or $C_{3-8}$ cycloalkyl group.

In a preferred set of compounds, $R^2$ is an optionally substituted $C_{1-4}$ alkyl group or $C_{3-8}$ cycloalkyl.

In another preferred set of compounds, $R^1$ and $R^2$ together form an optionally substituted $C_{3-8}$ cycloalkyl group. Most preferably this is a cyclopropyl group Other preferred compounds are those in which at least one of $R^1$ and $R^2$ is $-C(H)_n(F)_m$ or $-C(H)_n(F)_m-C(H)_p(F)_q$, where m=2 or 3, and n=(3-m); and p=2 or 3, and q=(3-p).

More preferably at least one of $R^1$ and $R^2$ is $CF_3$ or $CHF_2$. Most preferably, at least one of $R^1$ and $R^2$ is $CF_3$.

In an embodiment, $R^1$ is preferably methyl, cyclopropyl, $CF_3$ or $CHF_2$. More preferably, $R^1$ is methyl or cyclopropyl. Most preferably, $R^1$ is methyl. In an embodiment, $R^2$ is preferably methyl, cyclopropyl, $CF_3$ or $CHF_2$. More preferably $R^2$ is methyl or cyclopropyl. Most preferably $R^2$ is methyl.

In an embodiment:

$R^3$ and $R^4$ are independently selected from the group comprising: H; cyano; $C_{1-6}$ alkyl, $SC_{1-6}$ alkyl, $C_{2-6}$ alkenyl, $C_{2-6}$ alkynyl, $C_{3-8}$ cycloalkyl wherein said alkyl, alkenyl, alkynyl or cycloalkyl groups may be optionally substituted by 1 to 5 groups chosen independently from the group comprising: halo, hydroxyl, cyano, nitro, $C_{1-4}$ alkylsulphonyl and COOH; $C_{1-6}$ hydroxyalkyl; $C_{1-6}$ carboxyalkyl; and sulphide;

or $R^3$ and $R^4$ together with the carbon to which they are attached form a $C_{3-8}$ carbocyclic ring which may be optionally substituted by 1 to 5 groups chosen independently from the group comprising: halo, hydroxyl, cyano, nitro, $C_{1-4}$ haloalkyl, $C_{1-4}$ alkylsulphonyl and COOH;

or $R^3$ and $R^4$ together represent a $C_{2-6}$ alkenyl or $C_{2-6}$ alkynyl group bound through a double bond to the ring to which it is attached and which may be optionally substituted by one to three groups independently selected from the group comprising: halo, hydroxyl, cyano, $C_{1-4}$ haloalkyl and COOH.

In an embodiment, $R^3$ is H or $C_{1-6}$ alkyl. Preferably, $R^3$ is H.

In an embodiment $R^4$ is H or $C_{1-6}$ alkyl. Preferably, $R^4$ is H.

In an embodiment, $R^5$ is preferably chloro,

In an embodiment, $R^6$ is preferably chloro.

In an embodiment $R^7$ is H.

In an embodiment $R^8$ is H.

In an embodiment $R^9$ is H. In an alternative embodiment, $R^9$ is $C_{1-6}$ alkyl and, in this case, the PDE III inhibiting activity is effectively eliminated. Me represents a particularly preferred alkyl substituent. In another alternative embodiment, $R^9$ is a Group I metal ion and, in this case the compounds show significantly improved water solubility. Sodium represents a particularly preferred Group I metal.

In a further embodiment:

$R^1$ and $R^2$ are independently selected from the group comprising: H; cyano; $C_{1-6}$ alkyl, $C_{2-6}$ alkenyl, $C_{2-6}$ alkynyl, $C_{3-8}$ cycloalkyl wherein said alkyl, alkenyl, alkynyl or cycloalkyl groups may be optionally substituted by 1 to 5 groups chosen independently from the group comprising: halo, hydroxyl, cyano, nitro, $C_{1-4}$ alkylsulphonyl and COOH; $C_{1-6}$ hydroxyalkyl; $C_{1-6}$ carboxyalkyl; and sulphide;

or $R^1$ and $R^2$ together with the carbon to which they are attached form a $C_{3-8}$ carbocyclic ring may be optionally substituted by 1 to 5 groups chosen independently from the group comprising: halo, hydroxyl, cyano, nitro, $C_{1-4}$ haloalkyl, $C_{1-4}$ alkylsulphonyl and COOH;

or $R^1$ and $R^2$ together with the carbon to which they are attached represent a $C_{2-6}$ alkenyl or $C_{2-6}$ alkynyl group bound through a double bond to the ring to which it is attached and being optionally substituted by one to three groups independently selected from the group comprising: halo, hydroxyl, cyano, $C_{1-4}$ haloalkyl and COOH;

provided always that $R^1$ and $R^2$ are not both hydrogen, or that when one of $R^1$ and $R^2$ is methyl the other is not hydrogen;

$R^3$ and $R^4$ are hydrogen;

$R^5$ is selected from the group comprising: fluoro, chloro, bromo and iodo;

$R^6$ is selected from the group comprising: fluoro, chloro, bromo and iodo; and $R^7$, $R^8$ and $R^9$ are hydrogen.

Another preferred group of compounds is those in which neither $R^1$ nor $R^2$ is hydrogen. Amongst these, it is preferred when $R^1$ and $R^2$ are both independently selected from the group comprising: cyano, $C_{1-6}$ alkyl, $C_{2-6}$ alkenyl, $C_{2-6}$ alkynyl, in which the alkyl, alkenyl, and alkynyl groups may be optionally substituted;

or wherein $R^1$ and $R^2$ together with the carbon to which they are attached form an optionally substituted $C_{3-8}$ carbocyclic ring or wherein $R^1$ and $R^2$ together represent an optionally substituted $C_{2-6}$ alkenyl or $C_{2-6}$ alkynyl group.

Particularly preferred individual compounds of the invention include:

3-methyleneanagrelide 3,3,spiro-cyclopropyl-anagrelide 3,3-dimethylanagrelide (R)-3-(hydroxymethyl)anagrelide
(S)-3-(hydroxymethyl)anagrelide Particularly preferred compounds include 3,3-dimethylanagrelide, and spiro[anagrelide-3,1-cyclopropane]}. These compounds are generally prepared as the HBr addition salts.

It has also been found that the individual enantiomers of 3-substituted derivatives show efficacy. The present invention therefore also relates to both the resolved optical isomers of such compounds as well as mixtures of enantiomers. For the purposes of comparison of the compounds of the present invention with anagrelide, the correct comparison is that made with the PDE III inhibitory activity of the 3-hydroxy metabolite of anagrelide since this is the predominant component in plasma after anagrelide treatment.

Regarding the use of the compounds of the invention in humans, there is provided:
a pharmaceutical composition comprising a compound of formula (I), or a pharmaceutically acceptable salt or solvate thereof together with a pharmaceutically acceptable diluent or carrier, which may be adapted for oral, parenteral or topical administration;
a compound of formula (I), or a pharmaceutically acceptable salt or solvate thereof, or a pharmaceutical composition containing any of the foregoing, for use as a medicament;
the use of a compound of formula (I), or a pharmaceutically acceptable salt or solvate thereof in the manufacture of a medicament for the treatment of a disease selected from: mycloprolific diseases and/or generalised thrombotic diseases.
a method of treating a disease selected from: myeloproliferative diseases and/or generalised thrombotic diseases in a human, which comprises treating said human with an effective amount of a compound of formula (I), or a pharmaceutically acceptable salt or solvate thereof, or with a pharmaceutical composition containing any of the foregoing.

The present invention also encompasses a method of treating a patient having essential thrombocythemia or high blood platelet count, which method comprises administering to the patient a therapeutically effective amount of a compound of the present invention.

Another embodiment of the present invention includes a method of reducing blood platelet count within a patient, which method comprises administering to the patient a therapeutically effective amount of a compound of the present invention.

The present invention encompasses providing the compounds of the present invention for the methods listed above, among others, wherein cardiotoxicity is reduced compared to using anagrelide.

Separately, we have found that individually both (R)-3-methyl anagrelide and (S)-3-methyl anagrelide show good anti-megakaryocytic activity whilst showing significantly reduced PDE III inhibition relative to 3-OH anagrelide. We thus expect that 3-methyl anagrelide will have utility in treating myeloproliferative diseases.

Accordingly, the invention also includes the use of 3-methyl anagrelide, or a pharmaceutically acceptable salt or solvate thereof in the manufacture of a medicament for the treatment of myeloprolific diseases.

The invention thus also extends to a method of treating myeloproliferative diseases in a human, which comprises treating said human with an effective amount of 3-methyl anagrelide, or a pharmaceutically acceptable salt or solvate thereof, or with a pharmaceutical composition containing any of the foregoing.

The present invention also encompasses pharmaceutical compositions comprising a compound or pharmaceutically acceptable salt of a compound of the present invention and a pharmaceutically acceptable carrier.

DETAILED DESCRIPTION OF THE INVENTION

The present invention is directed to new 3 or 5-substituted analogues of the established platelet lowering agent anagrelide. Substitution at the 3 or the adjacent 5-position of the anagrelide molecule would be expected to block or hinder the principal site of metabolism and potentially preclude the formation of the highly potent PDE III inhibitor 3-OH anagrelide while substitution at the 1-position has surprisingly been found to abolish PDE III inhibition. The compounds of the present invention retain the anti-megakaryocytic properties (hence platelet lowering activity) of the parent drug molecule but have reduced PDE III inhibitory properties and hence lower potential for unwanted cardiovascular and anti-aggregatory side-effects. They also have the potential for improved pharmacokinetic characteristics as the result of inhibition of metabolism.

These improved cardiovascular and pharmacokinetic properties were demonstrated by studies in the dog. A comparison of the in vivo cardiovascular effects of anagrelide, its active metabolite and a representative example of an improved analogue shown in the table below:—

Comparative Activity of Anagrelide, its Metabolite 3-Hydroxy Anagrelide and a Representative 3-Alkyl Substituted Analogue of the Drug

| Compound | In vitro IC50 for PDE III inhibition (human enzyme) | In vivo ED50 for effects on dog heart rate | In vivo ED20 for effects on dog heart rate | In vitro IC50 for anti-megakaryocytic effects (human cell-line) |
|---|---|---|---|---|
| Anagrelide | 29 nM | 986 µg/kg | 376 µg/kg | 26 nM |
| 3-hydroxy anagrelide (active metabolite) | 0.7 nM | 11.72 ug/kg | 7.1 µg/kg | 44 nM |
| 3,3 dimethyl anagelide | 164 nM | 3,557 ug/kg | 2,512 µg/kg | 166 nM |

The most meaningful comparison of the data cited in the table above is between 3-hydroxy anagrelide—as the drug's active metabolite—and the 3-alkyl substituted analogue since the former is the predominant species present in the plasma of patients treated with the drug. On this basis the therapeutic benefit to potential for CV side effects ratio is clearly much improved for this 3-alkyl derivative.

A comparison of the pharmacokinetic profile in the dog of anagrelide and a representative 3-substituted analogue is shown below:—

Comparative Pharmacokinetics of Anagrelide, its Resultant Active Metabolite and a Representative 3-Substituted Analogue Follow 1 mg/kg iv in the Conscious Dog Model

| Compound | $C_{max}$ (ng/mL) | $AUC_{(0-t)}$ (ng · h/mL) | $T_{1/2}$ (h) | CL* (mL/h/kg) | $V_{ss}$* (mL/kg) | $F_{(AUC0-t)}$* |
|---|---|---|---|---|---|---|
| Anagrelide | 48.1 ± 21 | 101 ± 15 | 1.37 ± 20 | 1156 ± 4.56 | 1011 ± 3.8 | 11.8 ± 14.4 |
| 3-hydroxy anagrelide (arising from anagrelide treatment) | 60.1 ± 14 | 179 ± 14 | 1.57 ± 24 | NA | NA | |
| 3,3 dimethyl anagelide | 167 ± 33 | 1903 ± 47 | 9.39 ± 21 | 178 ± 45.9 | 1967 ± 24 | 39 ± 25 |

Results represent geometric means and % CV
*After 1 mg/kg iv

The data in the above table clearly show a much longer half-life for the 3-alkyl substituted analogue compared to anagrelide itself (9.39 vs 1.37 h) which, if reflected in man, should enable much less frequent drug administration and improved patient compliance compared to that seen with anagrelide. This comparatively longer half-life for 3,3 dimethyl anagrelide observed in the dog was mirrored in an in vitro metabolic stability study in which it was clearly much more metabolically stable than anagrelide (see table below). Hepatic metabolism is known to be the principal mechanism of clearance of anagrelide in both animals and in man. Furthermore, and most importantly, this much greater metabolic stability for the 3-substituted analogue was also observed in human hepatocytes suggesting the likelihood of improved pharmacokinetics in man.

Comparative Metabolic Stability of Anagrelide and a Representative Analogue in Dog and Human Hepatocytes

| Compound | In vitro "half-life" in dog hepatocytes | In vitro "half-life" in human hepatocytes |
|---|---|---|
| Anagrelide | 1.25 h | 6.62 h |
| 3,3 dimethyl anagrelide | No apparent degradation over time course of study | 22.8 h |

The pharmaceutically acceptable acid addition salts of certain of the compounds of formula (I) may also be prepared in a conventional manner. For example, a solution of the free base is treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties, Selection, and Use" by Stahl and Wermuth (Wiley-VCH, Weinheim, Germany, 2002).

DEFINITION OF TERMS

Halo means a group selected from: fluoro, chloro, bromo or iodo.

The term "alkyl" as used herein as a group or a part of a group refers to a straight or branched hydrocarbon chain containing the specified number of carbon atoms. For example, $C_{1-10}$ alkyl means a straight or branched alkyl containing at least 1 and at most 10 carbon atoms. Examples of "alkyl" as used herein include, but are not limited to, methyl, ethyl, n-propyl, n-butyl, n-pentyl, isobutyl, isopropyl, t-butyl, hexyl, heptyl, octyl, nonyl and decyl. A $C_{1-4}$ alkyl group is one embodiment, for example methyl, ethyl, n-propyl, isopropyl, n-butyl, isobutyl or t-butyl.

The term "cycloalkyl" as used herein refers to a non-aromatic monocyclic hydrocarbon ring of 3 to 8 carbon atoms such as, for example, but not limited to, cyclopropyl, cyclobutyl, cyclopentyl, cyclohexyl or cycloheptyl.

The term "spirocyclic" as used herein refers to a ring system joined to a second ring system at one carbon atom.

The term "alkoxy" as used herein refers to a straight or branched hydrocarbon chain group containing oxygen and the specified number of carbon atoms. For example, $C_{1-6}$ alkoxy means a straight or branched alkoxy containing at least 1 and at most 6 carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$ alkoxy group is one embodiment, for example methoxy, ethoxy, propoxy, prop-2-oxy, butoxy, but-2-oxy or 2-methylprop-2-oxy.

The term "hydroxyalkyl" as used herein as a group refers to a straight or branched hydrocarbon chain containing the specified number of carbon atoms, which is substituted by 1-3 hydroxyl groups. For example, $C_{1-4}$ hydroxyalkyl means a straight or branched alkyl chain containing from 1 to 4 carbon atoms and at least one hydroxyl group; examples of such group include hydroxymethyl, hydroxyethyl, hydroxypropyl, hydroxyisopropyl, hydroxybutyl and the like.

The term "alkenyl" as used herein as a group or a part of a group refers to a straight or branched hydrocarbon chain containing the specified number of carbon atoms and containing at least one double bond. For example, the term "$C_{2-6}$ alkenyl" means a straight or branched alkenyl containing at least 2 and at most 6 carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. It will be appreciated that in groups of the form —O—$C_{2-6}$ alkenyl, the double bond is preferably not adjacent to the oxygen.

The term "alkynyl" as used herein as a group or a part of a group refers to a straight or branched hydrocarbon chain containing the specified number of carbon atoms and containing at least one triple bond. For example, the term "$C_{2-6}$ alkynyl" means a straight or branched alkynyl containing at least 2 and at most 6 carbon atoms and containing at least one triple bond. Examples of "alkynyl" as used herein include, but are not limited to, ethynyl, 2-propynyl, 3-butynyl, 2-butynyl, 2-pentynyl, 3-pentynyl, 3-methyl-2-butynyl, 3-methylbut-2-ynyl, 3-hexynyl, and 1,1-dimethylbut-2-ynyl. It will be appreciated that in groups of the form —O—$C_{2-6}$ alkynyl, the triple bond is preferably not adjacent to the oxygen. The term "halo" refers to halogens such as fluorine, chlorine, bromine or iodine atoms.

The term "sulfide" refers to a radical of $R_a$—S—$R_b$, wherein a sulfur atom is covalently attached to two hydrocarbon chains, $R_a$ and $R_b$, wherein the two hydrocarbon chains may be, for example, but not limited to, any discussed above.

The compounds of the invention, i.e. those of formula (I), possess antimegakaryocytic activity in humans. They may be particularly useful in the treatment of myeloprolific diseases. The compounds may also find utility in the treatment of generalised thrombotic diseases.

It is to be appreciated that references to treatment include prophylaxis as well as the alleviation of established symptoms of a condition. "Treating" or "treatment" of a state, disorder or condition includes. (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

Myeloproliferative diseases which may be treatable with the compounds of the present invention include: essential thrombocythemia, polycythema vera, chronic idiopathic myelofibrosis, chronic myeloid leukaemia with residual thrombocytosis, reactive thrombocytosis immediately preceding a surgical procedures, as an immediate or post operative preventative measures to minimise the risk of thrombus formation during or post surgery.

Thrombotic cardiovascular diseases (TCVD) (i.e. patients at increased generalised thrombotic risk) which may also be treatable with the compounds of the present invention include: myocardial infarct (heart attack) thrombotic stroke, patients having undergone coronary stent placement.

The compounds of the present invention may find utility for the reduction of atherothrombotic events as follows: recent MI, recent stroke or established peripheral arterial disease, acute coronary syndrome (unstable angina/non-Qwave MI), cardiovascular death, MI, stroke, and refractory ischemia.

It is to be understood that compounds of formula (I) may contain one or more asymmetric carbon atoms, thus compounds of the invention can exist as two or more stereoisomers.

Included within the scope of the present invention are all stereoisomers such as enantiomers and diasteromers, all geometric isomers and tautomeric forms of the compounds of formula (I), including compounds exhibiting more than one type of isomerism, and mixtures of one or more thereof.

Solubility studies were carried out on a number of anagrelide derivatives according to the present invention in various test media. The test media were;
 a) singly distilled water (pH 5.0)—note no attempt was made to remove dissolved $CO_2$.
 b) 50 mM ammonium formate (pH 7.9)
 c) 0.1 M hydrochloric acid (pH 0.6)

Calibration plots of HPLC peak area vs. concentration were obtained in MeOH or MeOH/DMSO over the range 1000-1 µg/ml for each substance at a temperature 20-22° C. The HPLC method used a reverse phase $C_{18}$ column with a water (0.6% formic acid) and acetonitrile gradient. For the solubility studies, saturated solutions were prepared by dissolving in the desired medium with the aid of an ultrasonic bath for 20 minutes and the excess solid removed by centrifugation. The concentration of the substance in the supernatant liquid was determined from the measured peak area.

Unexpectedly it was found that stable metal salts could be prepared following deprotonation at the 1-position of the quinazoline ring structure. The value of such salts is seen in their relatively much greater aqueous solubility than the corresponding HBr salts. This is likely to facilitate the rapid dissolution and quantitative absorption of these generally poorly water soluble compounds and so represent a major clinical advantage. These salts are Group I metal salts and most usually are sodium or potassium salts. Table 1 shows the results of the solubility measurements.

TABLE 1

Solubilities of Anagrelide and Anagrelide Derivatives (µg mL$^{-1}$ at ca. 20° C.)

| Compound | Ammonium formate (50 mM, pH 7.9) | Water (pH 5.0) | Hydrochloric acid (0.1M, pH 0.6) |
|---|---|---|---|
| Anagrelide hydrochloride | 10 | 11 | 169 |
| 3,3-Dimethylanagrelide sodium salt | 6 | 409 | 212 |
| 3,3-Dimethylanagrelide hydrobromide | 4 | 20 | 215 |
| 3,3,Spiro-Cyclopropyl-anagrelide sodium salt | 1 | 542 | 28 |
| 3,3-spiro-Cyclopropyl-anagrelide hydrobromide | 1 | 2 | 35 |
| 3-Methyleneanagrelide | 5 | 9 | 43 |
| 3-Methyleneanagrelide Na salt | 39 | 1830 | 189 |

Geometric isomers may be separated by conventional techniques well known to those skilled in the art, for example, by chromatography and fractional crystallisation.

Stereoisomers may be separated by conventional techniques known to those skilled in the art—see, for example, "Stereochemistry of Organic Compounds" by E L Eliel (Wiley, New York, 1994).

The compounds of formula I can be prepared using literature techniques and in an analogous manner to those described in Formula Scheme I and Formula Scheme II in U.S. Pat. No. 4,256,748. The synthesis of 3-ethyl anagrelide is described by way of example to show how individual isomers of the invention can be prepared. Analogous procedures can be used to prepare the other compounds of the invention by using appropriate α-haloesters The formation of 3-ethyl anagrelide (compound (4a)) is shown in Scheme A below. 1-amino-2,3-dichloro nitrobenzene (1a) undergoes nucleophilic substitution with the α-haloester R-ethyl-2-bromobutanoate to afford compound (2a). The nitro group is then reduced to an amine group using tin chloride in ethanol to afford the diamine compound (3a). Compound (3a) is then cyclised with cyanogen bromide in toluene to yield the 3-ethyl anagrelide (4a).

Scheme A:
Formation of 3-ethylanagrelide.

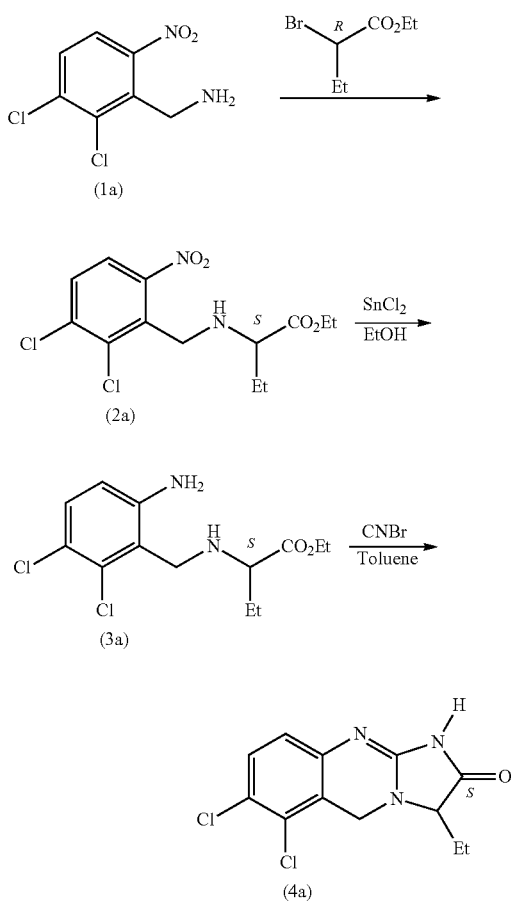

The formation of certain derivatives is accomplished in an analogous manner to the synthesis shown in Scheme A above or by reversing the positions of the NH$_2$ group and the Br groups in the starting materials, as appropriate to the chemistry involved. In this case, an α-aminoester and a halobenzyl derivative are used as the starting materials. The reaction can be generically presented as shown in Scheme B below in relation to the 3-substituted compound.

Scheme B:
Formation of 3-substituted anagrelides.

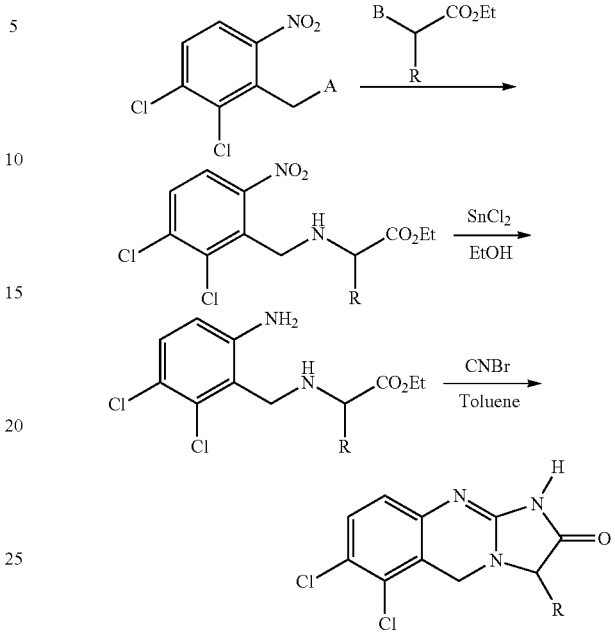

where A is NH$_2$ or Br, and B is the other of NH$_2$ or Br

The formation of (R)-3-ethyl anagrelide can be accomplished in an analogus manner to the synthesis shown in Scheme A above. In this case an α-haloester of the opposite stereochemistry to that used in Scheme A is employed in the nucleophilic substitution step i.e. S-ethyl-2-bromobutanonate. This procedure is generally applicable.

If single enantiomers are not required then a racemic α-haloester can be employed in the first stage of the synthesis.

A person skilled in the art will be aware of variations of, and alternatives to, the processes referred to above and to those in U.S. Pat. No. 4,256,748 which allow the individual compounds defined by formula (I) to be obtained.

It will also be appreciated by a person skilled in the art that the compounds of the invention could be made by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

It will also be apparent to a person skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs. Generally, they will be administered as a formulation in association with one or more pharmaceutically acceptable excipients. Pharmaceutically acceptable excipients include one or more of: anti-oxidants, colourants, flavouring agents, preservatives and taste-masking agents.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995). The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The methods by which the compounds may be administered include oral administration by capsule, bolus, tablet, powders, lozenges, chews, multi and nanoparticulates, gels, solid solution, films, sprays, or liquid formulation. Liquid forms include suspensions, solutions, and syrups. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid preparation, for example, from a sachet.

The compounds may also be administered topically to the skin or mucosa, that is dermally or transdermally. Typical formulations for this purpose include pour-on solutions, sprays, powder formulations, gels, hydrogels, lotions, creams, ointments, films and patches, and implants.

The compounds can also be administered parenterally, or by injection directly into the blood stream, muscle or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Formulations may be immediate and/or modified controlled release. Controlled release formulations include Modified release formulations include: delayed-, sustained-, and pulsed-release.

Dosages

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

In general however a suitable dose will be in the range of from about 0.001 to about 50 mg/kg of body weight per day, in a further embodiment, of from about 0.001 to about 5 mg/kg of body weight per day; in a further embodiment of from about 0.001 to about 0.5 mg/kg of body weight per day and in yet a further embodiment of from about 0.001 to about 0.1 mg/kg of body weight per day. In farther embodiments, the ranges can be of from about 0.1 to about 750 mg/kg of body weight per day, in the range of 0.5 to 60 mg/kg/day, and in the range of 1 to 20 mg/kg/day.

The desired dose may conveniently be presented in a single dose or as divided doses administered at appropriate intervals, for example as one, two, three, four or more doses per day. If the compounds are administered transdermally or in extended release form, the compounds could be dosed once a day or less.

The compound is conveniently administered in unit dosage form; for example containing 0.1 to 50 mg, conveniently 0.1 to 5 mg, most conveniently 0.1 to 5 mg of active ingredient per unit dosage form. In yet a further embodiment, the compound can conveniently administered in unit dosage form; for example containing 10 to 1500 mg, 20 to 1000 mg, or 50 to 700 mg of active ingredient per unit dosage form.

Compounds of the present invention and their activities are exemplified below.

Example 1

Comparative $IC_{50}$ Data on Anagrelide and Some 3-Alkyl Substituted Analogues as PDE III Inhibitors and Anti-Megakaryocytic Agents The table below shows the comparative activity of anagrelide and its analogues with respect to their effects on megakaryocytopoeisis (the process giving rise to blood platelets) and PDE III (inhibition of which leads to adverse cardiovascular responses).

Comparative in vitro Assessment of Potential Therapeutic and Adverse Effects of Anagrelide and its Analogues

| Compound | $IC_{50}$ for anti-megakaryocytic (platelet lowering) activity | $IC_{50}$ for PDE III inhibition (cardiovascular effects) | Benefit ratio (therapeutic to adverse effects) |
|---|---|---|---|
| Anagrelide | 27 nM | 32 nM | *0024:1 |
| 3-hydroxy anagrelide | 44 nM | 0.7 nM | 0.016:1 |
| 3,3 dimethyl anagrelide | 164 nM | 166 nM | 1:1 |
| 3-spirocyclo propyl anagrelide | 547 nM | 797 nM | 1.45:1 |

*Pharmacokinetically adjusted value based on three-fold greater systemic exposure to active metabolite (3-hydroxy anagrelide) than to the drug itself in man.

Assessment of the in vitro anti-megakaryocytic activity—and potentially therefore the platelet lowering capability—of the 3-substituted analogues of anagrelide was conducted using a well established model of megakaryocytopoiesis (Cohen-Solal et at, Thromb. Haemost. 1997, 78:37-41 and Cramer et al, Blood, 1997, 89:2336-46). It can be readily seen that with anagrelide the benefit ratio (therapeutic to adverse effects) was comparatively low at 0.024:1 (after accounting for the predominant exposure to the cardioactive metabolite in vivo). By contrast 3-spirocyclopropyl and 3,3 dimethyl anagrelide both demonstrated a relatively much better benefit ratio in these studies.

The invention claimed is:

1. 3,3-dimethylanagrelide or a pharmaceutically acceptable salt thereof.

2. A pharmaceutical composition comprising 3,3-dimethylanagrelide or a pharmaceutically acceptable salt thereof, together with a pharmaceutically acceptable diluent or carrier.

3. The pharmaceutical composition of claim 2, wherein the pharmaceutical composition is suitable for oral administration.

4. The pharmaceutical composition of claim 2, wherein the pharmaceutical composition is a unit dosage form, and the unit dosage form comprises 0.1 to 50 mg of 3,3-dimethylanagrelide or a pharmaceutically acceptable salt thereof.

5. The pharmaceutical composition of claim 2, wherein the pharmaceutical composition is a unit dosage form, and the unit dosage form comprises 0.1 to 5 mg of 3,3-dimethylanagrelide or a pharmaceutically acceptable salt thereof.

* * * * *